United States Patent [19]

Ye et al.

[11] Patent Number: 5,547,945
[45] Date of Patent: Aug. 20, 1996

[54] REMITTING AGENT FOR NEPHROTIC SYNDROME AND HEPATOPATHY SYMPTOMS

[75] Inventors: Guoji Ye; Jun-ichi Kajihara, both of Kobe; Sei Kirihara, Miki; Kazuo Kato, Kobe; Hiroko Abe, Sakai, all of Japan

[73] Assignee: JCR Pharmaceuticals Co., Ltd., Hyogo, Japan

[21] Appl. No.: 271,795

[22] Filed: Jul. 7, 1994

[30] Foreign Application Priority Data

Jul. 15, 1993 [JP] Japan .................................. 5-199275
Mar. 30, 1994 [JP] Japan .................................. 6-085871

[51] Int. Cl.$^6$ ........................ A61K 31/715; C08B 37/06; C07H 1/00; C07H 1/08
[52] U.S. Cl. .............................. 514/54; 536/2; 536/123; 536/124; 536/128
[58] Field of Search .......................... 536/2, 123, 124, 536/128; 514/54

[56] References Cited

U.S. PATENT DOCUMENTS 4,225,592  9/1980  Lakatos et al. .......................... 536/121
4,689,322  8/1987  Kulbe et al. ............................... 514/54

OTHER PUBLICATIONS

Plana Medica, vol. 0, No. 4, issued 1985, Braeutigam et al, "Structural Features of Plantago-Lanceolata Mucilage", pp. 293-297.

Planta Medica, vol. 49, No.3, issued 1983, Kram et al., "Analysis of Linden Tilia-SP Flower Mucilage", pp. 149-153.

Primary Examiner—John Kight, III
Assistant Examiner—Everett White
Attorney, Agent, or Firm—Burgess, Ryan and Wayne

[57] ABSTRACT

A remitting agent for nephrotic syndrome and hepatopathy symptoms is provided that which comprises water-soluble polysaccharides having poly-D-galacturonic acid as an effective constituent; polysaccharides having the following characteristic properties which are extractable from Tanjin with water or an aqueous solvent:

A. Sugar content: 60 to 100%.
(1) Sugar composition:
  40 to 80% of uronic acid (composed almost entirely of D-galacturonic acid) and
  10 to 30% of neutral sugars
(2) Neutral sugar composition:
  0 to 15% of rhamnose
  0 to 15% of glucose
  25 to 55% of galactose
  30 to 60% of arabinose
  0 to 15% of mannose B. Molecular weight: 150,000 to 300,000; the invention also provides a process for producing the above-described polysaccharides which comprises allowing an aqueous extract of Tanjin to pass through a porous polymeric resin, followed by purification through gel filtration chromatography.

7 Claims, 4 Drawing Sheets

REMITTING AGENT FOR NEPHROTIC SYNDROME AND HEPATOPATHY SYMPTOMS

BACKGROUND OF THE INVENTION

1) Field of the Invention

The present invention relates to a safe therapeutic agent for oral and intramuscular application which can be administered to patients diagnosed as being afflicted with renal diseases, among others nephrotic syndrome, and patients with hepatic disorders such as viral or drug-induced heptitis, thereby permitting such patients to attend hospitals as an outpatient. Special attention should be directed to the facts that such renal diseases in recent years tend to occur with greater frequency not only in the senile but also young generations and that the nephrotic syndrome is considered to be a step of inducing chronic renal insufficiency.

2) Background of the Invention

As an internal therapeutic drug for lipoid nephrosis or minimal change nephrotic syndrome, there have been employed chemically synthesized steroids or dipyridamole, a antiplatelet drug, which however require prolonged administration and, upon application to the younger generation, are accompanied with great apprehension for the onset of side effects, such as full-moon face, menstrual disorders, dizziness, headache, nausea and vomiting, as well as, in the serious cases, infections, gastrointestinal bleeding, metabolic disorders, osteoporosis, thrombosis, adrenal insufficiency and mental disorders.

Hepatitis, which disease is roughly classified into the viral and drug-induced types, occurs mostly in the form of viral type, and the biological response modifiers (hereinafter referred to briefly as "BRMs"), for example interferons and interleukin 2, and Minofagen C, an intravenous injectable preparation of glycyrrhizin, are put in clinical use as a treatment agent against hepatitis. Nevertheless, BRMs are found to cause side effects such as fever, and encounter difficulties in consecutive administration over an extended period of time, while glycyrrhizin, belonging essentially to an anti-inflammatory agent, requires the management of hypertension and electrolytes for the prolonged administration. In addition to these, Saikosaponin, saponin, Gomishin, etc. are known but have never put into clinical application so far.

As water-soluble polysaccharides having poly-D-galacturonic acid of the following formula (I):

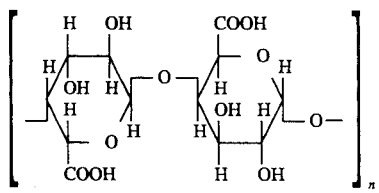

(wherein the carboxyl group(s) may be esterified with methyl), there are known, for example, pectic substances which are water-soluble polysaccharides composed mainly of poly-D-galacturonic acid being obtained by extracting the fruit rinds of oranges with an acidic aqueous solution, effecting demethylation with an acid, alkali or enzyme, and then precipitating by adding organic solvent such as alcohols. The water-soluble pectic substances are grouped into pectin and pectinic acid according to the degree of methyl esterification of the carboxyl groups in the poly-D-galacturonic acid, whereas the counterpart being substantially free from any methyl ester remained is called pectic acid.

Water-soluble pectic substances are mainly used in the food industry as a starting material for jellies, etc. but have hardly found application as a pharmaceutical except that they are employed to cover the mucous membranes.

The present invention, in one aspect, utilizes the extracted component of Tanjin. Tanjin is a medical plant that has been traditionally used in China for its efficacies of improving blood circulation and ameliorating the blockade of blood circulation. With regard to Tanjin, in recent years, many reports have been published in Japan and abroad on their various pharmacological activities, for example, vasodilating activity (Hikoyoshi Ohura: Wakan Iyaku Gakkai-shi (Journal of the Society of Japanese-Chinese Drugs Association), 5: 227–237, 1988), hypotensive activity (Nakayama Igakuin-ron, published by Ishiyaku Shuppan Co., Tokyo, 257–258, 1980), inhibitory activity against blood coagulation (Koui Ra: Acta Pharmaceutica Sinica, 23 (11); 830–834, 1988), inhibitory activity against intracellular cholesterol synthesis (Sun Xi-ming; Chu-Yaku-Soh (Chinese Medical Plants), 22 (1): 20–23, 1991), hepatocyte protecting activity (I Shinko et al: Chuh-Sei-I Ketsugo Zasshi (Chinese-Western Medicine Conjugating Gazette): 11 (2), 102–104, 1991) and radical scavenging activity (Ko Tenki: Journal of Shanghai Chinese Drugs Association, 9: 28–30, 1988), as well as on the improvement of renal function (Hikoyoshi Ohura: Proceedings of the 2nd Chinese-Japanese Symposium on Medical and Pharmaceutical Research on Japanese-Chinese Drugs: pp.148–157, 1988) and efficacy in patients with chronic renal diseases and uremia (Cho Kyohjin: Journal of Shanghai Chinese Drug Association, 1, 17–18, 1981). However, these reports mentioned nothing on the identification of active substances showing such activities or efficacies, except the low-molecular-weight substances which differ entirely from what the present invention refers to.

At the same time, extensive research activities have been under way on the therapeutic drugs for renal diseases based on Tanjin, resulting for example in isolation of tansinone homologs that belong to low-molecular-weight phenanthrenequinones and magnesium lithosperminate B, a tetramer of caffeinic acid (T. Yoozawa, H. Y. Chung, H. Oura, G. Nagaoka and I. Nishioka; Chem. Pharm. Bull., 36, 316 (1988)), all of which are highly lipo-soluble substances obtained by extraction with solutions containing organic solvents and have not yet found clinical application.

Renal or kidney diseases can be roughly classified into the primary type involving the glomeruli and the secondary type originating from other diseases, with the former accounting for more than 80% of total onset and occurring more frequently in the younger generation, being occupied by about 90% of the occurrence. From the standpoint of histopathological findings, the diseases are grouped into minimal change nephrotic syndrome, glomerulosclerosis, membranous nephritis, mesangial proliferative glomerulonephritis (IgA nephritis and non-IgA nephritis), membranous proliferative glomerulonephritis, crescent-forming glomerulonephritis, etc. Proteinuria is observed as a clinical finding commonly among all histopathological types of diseases, whereby the serious proteinuria leads to the diagnosis as a nephrotic syndrome. Since the kidney diseases, especially those induced by the organic degeneration of the kidney, are taking place increasingly not only in the old or senile but also younger generations, furthermore, there is a strong demand for the development of a water-soluble drug based on a plant component having reduced side effects which is able to be administered to patients orally or intramuscularly to treat the disorders through organic amelioration.

On the other hand, hepatitis, which is roughly categorized into the viral type and the type induced by drugs such as alcohol, is caused overwhelmingly by infection with hepatitis B and C viruses. Nowadays, it has been reported that interferon is particularly effective in treating the hepatitis C, with its application becoming more frequent (S. Iino et al.: "Kiso to Rinsho" (Fundamental and Clinical), 26, 339, 1992; H. Suzuki et al.: "Kan.Tan.Sui" (Liver. Gallbladder-.Pancreas); 23, 1065, 1991). However, interferon, when applied for a short period of time, is found to cause influenza-like symptoms such as fever, while in the case of prolonged administration, it is noted to bring about adverse effects such as loss of weight, diarrhea, vomiting, arrhythmia, depilation and abnormalities in autoimmunity. In the light of the fact that the conventional drugs are in the form of injectable solution, there is a strong demand for the development of a simple and practically employable, novel therapeutic agent or a water-soluble medicine based on a plant drug or a component of a medical plant causing reduced side effects, which medicine is able to be administered patients orally or intramuscularly as a supplementary drug in combination with interferon, etc. for the treatment of hepatitis.

The present inventors conducted intensive investigation into such a drug substance on the basis of the widely employed nephrotic syndrome model realized in rats by puromycin which is well known to generate markedly proteinuria and to exhibit organic changes in the kidney, and as a result, found that the aqueous extract of Tanjin contains the polysaccharides which is effective for the above-described model and that the polysaccharides are composed mainly of poly-D-galacturonic acid.

SUMMARY OF THE INVENTION

The present invention, growing out of the above finding, relates to (I) a remitting agent for nephrotic syndrome and hepatopathy symptoms which comprises water-soluble polysaccharides having poly-D-galacturonic acid as an effective constituent, (II) to polysaccharides which can be extracted from Tanjin with water or an aqueous solvent and have the following characteristic properties:

A. Sugar content: 60 to 100%
(1) Sugar composition:
   40 to 80% of uronic acid (composed almost entirely of D-galacturonic acid) and
   10 to 30% of neutral sugars
(2) Neutral sugar composition:
   0 to 15% of rhamnose
   0 to 15% of glucose
   25 to 55% of galactose
   30 to 60% of arabinose
   0 to 15% of mannose B. Molecular weight: 150,000 to 300,000, and to (III) a process for producing a polysaccharide as described above, characterized in that said process comprises extracting the root or rhizome of Tanjin. with water or an aqueous solvent, passing a solution, as obtained by removing the residue from the extract, through a non-polar, porous polymeric resin, concentrating the eluate by means of ultrafiltration and then subjecting the concentrate to gel filtration chromatography.

DETAILED DESCRIPTION OF THE INVENTION

The water-soluble polysaccharides having a polygalacturonic acid as an effective constituent, as used, are water-soluble pectic substances being generally extractable from plants, and may be either pectins having not less than about 7.5% of carboxylic acids in galacturonic acid methyl-esterified, pectins with a reduced degree of methyl esterification or pectinic acids having practically entire methyl esters hydrolyzed. Generally, such water-soluble pectic substances often contain slight amounts of arabane, galactan, rhamnose, etc., but an be utilized as such.

The water-soluble polysaccharides of the present invention, as used, also include water-soluble pectic substances which are extracted for example from Tanjin.

The term "Tanjin" usually means the root or rhizome of Salviae miltiorrhizae Randix, but there may also be used the roots of the plants of the same genus, such as Salvia bowleyana Dunn, Salviar przewalskii Maxim and Salviae yunnanensis C. H. Wright. In the present invention, such plant species are collectively called "Tanjin".

Although no particular limitation is posed on the habitat of Tanjin as employed in this invention, Tanjin as produced in Szuchuan, China can preferably be used to extract and purify efficiently the polysaccharides of the present invention.

Tanjin is desirably reduced to pieces as small as possible for extraction, and water or aqueous solvents are used as a extraction solvent, wherein as the aqueous solvent, there are preferably used buffers such as phosphate buffers and acetate buffers, or solutions of sodium chloride or otehr salts.

It is desirable to adjust a pH value of the extraction solvent to about 2 to 9, and the extraction is preferably effected at a temperature of 50° to about 100° C., desirably 70° to 90° C. For example, Tanjin is placed in warm water heated in advance at 50° to 100° C. preferably 70° to 90° C. or a buffer or a solution of a salt having a pH value in the range of 2 to 9. or thereafter, heating is effected up to the desired temperature in a water bath, etc. to conduct extraction.

By this procedure, extraction is carried out for 1 to 8 hours, preferably 3 to 5 hours, to give a crude extract. The residual root or rhizoid contained in the extract can be filtered out through a coarse filter cloth or Buchner funnel.

The extract having the residue removed is further purified by means of column chromatography packed with a non-polar porous polymeric resin equilibrated with water. As the polymeric resin, there may be mentioned for example HP-20 and MCI-Gel (produced by Mitsubishi Chemical Industries, Ltd.) and Amberlite XAD-2 (produced by Organo Co.).

With regard to the active ingredient of Tanjin, a report was published on magnesium lithosperminate, a low-molecular-weight substance, which was eluted with a 50% methanol solution from a fraction obtained by adsorption fractionation on MCI-Gel, and the present inventors also confirmed that the similar fraction exhibits suppressory activity against discharge of proteinuria. In addition, testing was done with every eluted fractions inclusive of the non-adsorbed one to determine precisely their suppressory activity against discharge of proteinuria, and as a result, it was found that, contrary to what had originally been expected, even the freely passed effluent fraction contained the active ingredient exhibiting the above activity. At this point of time, the freely passed effluent fraction was assumed to be low in polarity and actually did not show any absorption spectra in the ultraviolet region peculiar to the protein, which suggested that the fraction was composed of something other than protein.

A portion of the freely passed effluent fraction was then passed through a system comprising two ultrafiltration membranes (with respective molecular weight cutoffs of 300,000 and 50,000) to investigate the concentration and purification steps. Namely, the fraction was divided into the three substance groups having individually a molecular weight range of not less than 300,000, 50,000 to 300,000 and less than 50,000, which were tested for suppressory activity against discharge of proteinuria with use of puromycin-induced nephrotic syndrome model in rats. As a result, the potent activity was revealed in the fraction having a molecular weight in the range of 50,000 to 300,000, with the weak activity being noted in the one with a molecular weight of less than 50,000.

In the light of the above, the freely passed effluent fraction was concentrated with use of a ultrafiltration membrane having a molecular weight cutoff of 3,000. In the concentration step for the substance of the present invention, any types of ultrafiltration membranes can be employed only if they have the equivalent molecular-weight cutoff size.

Then, the concentrated fraction was purified by means of gel permeation chromatography in order to identify the active ingredient contained in the concentrate as a substance with a narrow molecular weight range. In the chromatographic procedure for the substance of the present invention, there can be used Sephadex and Sepharose series products (produced by Pharmacia Co.), Selurofine (produced by Seikagaku Kogyo K.K.), Biogel (produced by Biorad Co.), etc. which are generally utilized as a carrier for gel permeation chromatography for purification of proteins and the like, and the carrier for chromatographic uses being prepared by the chemically synthetic means, such as Bio-Gel, are preferably suited for the purification of the substance of the present invention. There are various types of chromatographic packings having a different mesh size, or a various limit of exclusion, but any of such chromatographic packings may be employable only if they permit fractionation in the range of 10,000 to 300,000. The present inventors preferred the utilization of Bio-Gel P- 30, -60 and -100, among others, Bio-Gel P-60, and the concentrate was passed through a column packed with Bio-Gel 60 equilibrated with water, while monitoring the eluates provisionally by means of absorption at a wavelength of 280 nm. The fractions, which showed and did not show the absorption, were divided into several fractions of a volume up to twice that of the column and tested for the suppressory activity against the discharge of proteinuria in the puromycin-induced model in rats, leading to the finding that polysaccharides showing the activity were eluted in the high-molecular-weight range fractions.

The polysaccharides, when treated through oxidation with periodic acid or reduction, lose the activity, while they possess platelet aggregation inhibitory and erythrocyte membrane protective activities, as demonstrated by the in vitro testing. Though the radicals are known to be involved in the puromycin-induced nephrosis model or carbon-tetrachloride induced nephritic disorder model in rats, furthermore, the experiment with ESR showed that the polysaccharides possess no direct radical-scavenging action.

The polysaccharides, obtained by purifying (fractionation-purification) the extract from Tanjin by means of chromatography on a non-polar porous polymeric resin and gel permeation chromatography, were tested for their characteristic properties as described in the following:

(1) Total sugar content:
The phenol-sulfuric acid method (Hodge, J. E. and Hofreiter, B. T. (1962), Methods in Carbohydrate Chemistry (Academic Press), vol. 1, p. 338)

A 0.5 ml portion of a test solution was pipetted out in a test tube, to which 0.5 ml of 5% (v/v) phenol solution was added, and 2.5 ml of conc. sulfuric acid was added directly on the surface of the solution; the solution was stirred thoroughly and maintained at room temperature for 20 min, followed by measurement of absorbance at a wavelength of 480 nm, with an aqueous glucose solution (10 to 90 µg/ml) being used as a standard.

(2) Uronic acid content:
The m-hydroxydiphenyl method (Blumenkarantz, N. and Asboe Hansen, G. (1973), Anal. Biochem., 54, 484–489).

A 0.2 ml portion of a test solution was admixed with 1.2 ml of a 0.0125M solution of sodium borate in conc. sulfuric acid, followed by ice-cooling and stirring. The reaction solution is treated at 100° C. for 5 min., then cooled with ice and admixed with 20 µl of a 0.15% solution of m-hydroxydiphenyl in 0.5% sodium hydroxide solution, followed by measurement of absorbance at a wavelength of 520 nm, with a galacturonic acid solution being used as a standard.

(3) A neutral sugar content:
The Alditol acetate GC-MS method (Borchardt, L. G. and Piper, C. V. 91970), Tappi, 53, 257–260).

A 50 mg quantity of the purified fraction of the extract from Tanjin is dissolved in 3 ml of 72% (v/v) sulfuric acid and treated at 30° C for 1 hr., and the solution is admixed with 84 ml of distilled water, followed by autoclaving at 120° C. for 1 hr. and addition of 4 mg of inositol as an internal standard. 30 ml of the solution was adjusted to a pH value of 5.5 with barium hydroxide and centrifuged to give a supernatant fluid. 25 ml of the supernatant fluid is admixed with 80 mg of sodium borohydride, and the mixture is treated at room temperature for 2 hours, followed by addition of acetic acid to stop the reaction. The solution is concentrated, and the concentrate is dissolved in distilled water, followed by pouring into a DEAE Sephadex column to collect the freely passed effluent fractions. The fractions are concentrated, and the concentrate is subjected to acetylation with acetic anhydride and pyridine, followed by extraction with a solution mixture of dichloromethane and 1N hydrochloric acid. The organic layer is washed with distilled water and concentrated, and the concentrate is dissolved in acetone for quantitative determination by the gas chromatography-mass spectrometry (GC-MS) (column: a Supelco capillary column for sugar analysis). The standard product is subjected to the reduction treatment as described above and analyzed by the same procedures.

(4) Determination of molecular weight
A 10 µl portion of a test solution of the substance of the present invention is subjected to a Tosoh HPLC column (manufactured by Tosoh Inc.) being connected with an Asahi Pack GS-520 (manufactured by Asahi Chemical Industries, Ltd.) column (of 7.6 mm ID and 500 mm L) with use of Milli Q water to determine the molecular weight (temp.: room temperature, flow rate; 0.5 ml/min., detection: RID). As a MW marker, there are used amylose kits with individual molecular weights of 10,200, 30,100, 75,200, 111,400 and 364,200, and from the calibration curve prepared on the basis of these elution patterns, the molecular weight of the present substance is determined.

(5) Assessment with the puromycin-induced nephrotic syndrome model in rats:
1) Preparation of nephrotic syndrome model rats:
Female rats (about 9-weeks aged, weighing about 150 g) of Wistar strain were given a single dose of 60 mg of puromycin amino nucleoside (hereinafter refereed to briefly as "puromycin", supplied by Sigma Co.) through the carotid artery to prepare the nephrotic syndrome model; rats (S. Tohzyo et al.: "Nephrotic Syndrome", compiled by M. Kyogoku. Published by Soft Science Shuppan K.K. of Japan, 479–488, 1984).

2) Administration of the test solutions:

For 21 consecutive days starting with the day of administration of puromycin aminonucleoside, each of the test solutions was given the model rats orally through the stomach cannula or intramuscularly once a day, with purified water for injection and dipyridamole solution being given the negative and positive control groups, respectively.

3) Determination of urinary protein level:

A urinary protein was determined by the following procedure: the 24-hours urines were taken by use of a rat metabolism cage at the interval of 2 to 3 days as from Day 5 after administration of puromycin aminonucleoside to thereby measure their volumes, and then 1 ml of the supernatant fluid as obtained from each urine sample by centrifugation (3,000 rpm×10 min) was admixed with 3 ml of sulfosalicylic acid. The solution was left on standing at room temperature for 10 min and subjected to measurement of absorbance at a wavelength of 660 nm to determine a urinary protein level from the calibration curve. The total amount of protein excreted in the urine was calculated by multiplying the urinary protein level with the volume of the urine. Bovine serum albumin (produced by Sigma Chemical Co.) was used as a standard protein in preparing the calibration curve.

4) Determination of the serum cholesterol, serum albumin, total serum protein and serum peroxylipid levels:

On Days 7, 14 and 21 after administration of puromycin aminonucleoside, blood samples were drawn through the vein from rats of each group under anesthesia with ether to determine the contents of cholesterol, albumin, total protein and peroxylipid in the serum (used reagents as supplied by Wako Pure Chemicals).

(6) Assessment with carbon-tetrachloride induced liver-injury model in rats:

1) Preparation of liver-injury model rats:

Female, Wistar rats (9 to 11 weeks aged, weighing about 160 g) were given a 1:1 mixture of carbon tetrachloride (produced by Wako Pure Chemicals) and olive oil intraperitoneally once at a dose of 1.5 ml/kg to prepare the liver-injury model (Enshohgaku-Sho: Experimental Methods with Inflammatory Animals, Experimental Hepatic Fibrosis. Published by Igaku Shoin, 253–277).

2) Administration of the test solutions:

Each of the test solutions was given the treated groups intramuscularly once a day over the 3 days period of from Days 3 to 1, or orally once a day over the 7 days period of from Days 7 to 1, before administration of carbon tetrachloride, with the purified water for injection being given the negative control group.

3) Biochemical test of serum:

Blood samples in the volume of 2 ml were drawn from the rats through the heart, as subjected to thoracotomy under anesthesia with ether, then left on standing at room temperature and centrifuged to give serums, which were assayed for serum transaminase activity (GOT: glutamic oxaloacetic transaminase, GOT; glutamic pyruvic transaminase) by use of the testing kit manufactured by Wako Pure Chemicals Ind.

4) Statistical analysis:

The measured data were expressed as the mean ±S.E. and analyzed by the student's t-test.

As is indicated in the below-described examples, in the animal experiments, the polysaccharides of the present invention are effective for remitting the nephrotic syndrome and improving the hepatopathy symptoms, and therefore can normally be administered to human adults, as a remitting agent for nephrotic syndrome or an improving agent for hematopathy symptoms, orally at a daily dose of about 10 to 150 mg, or intramuscularly at a daily dose of about 0.5 to 10 mg.

Below described are the examples and test examples to illustrate the present invention in more detail.

EXAMPLE 1

To 10 kg of small pieces of the root of Salviae miltiorrhizae Radix as grown in Sechwan, China was added 30 liters of water, and the mixture was heated at 80° C. with use of an immersion heating placed therein, followed by extraction for 3 hours under stirring. The root residue in the extract were separated through filtration with Nutsche, and the recovered root residue was treated with 80 liters of water added once again in the same manner as described above to give the second extract. The first and second extracts (130 liters) were combined and concentrated at 40° C. under reduced pressure with use of an evaporator to give a concentrate (10 liters).

Figure 1:
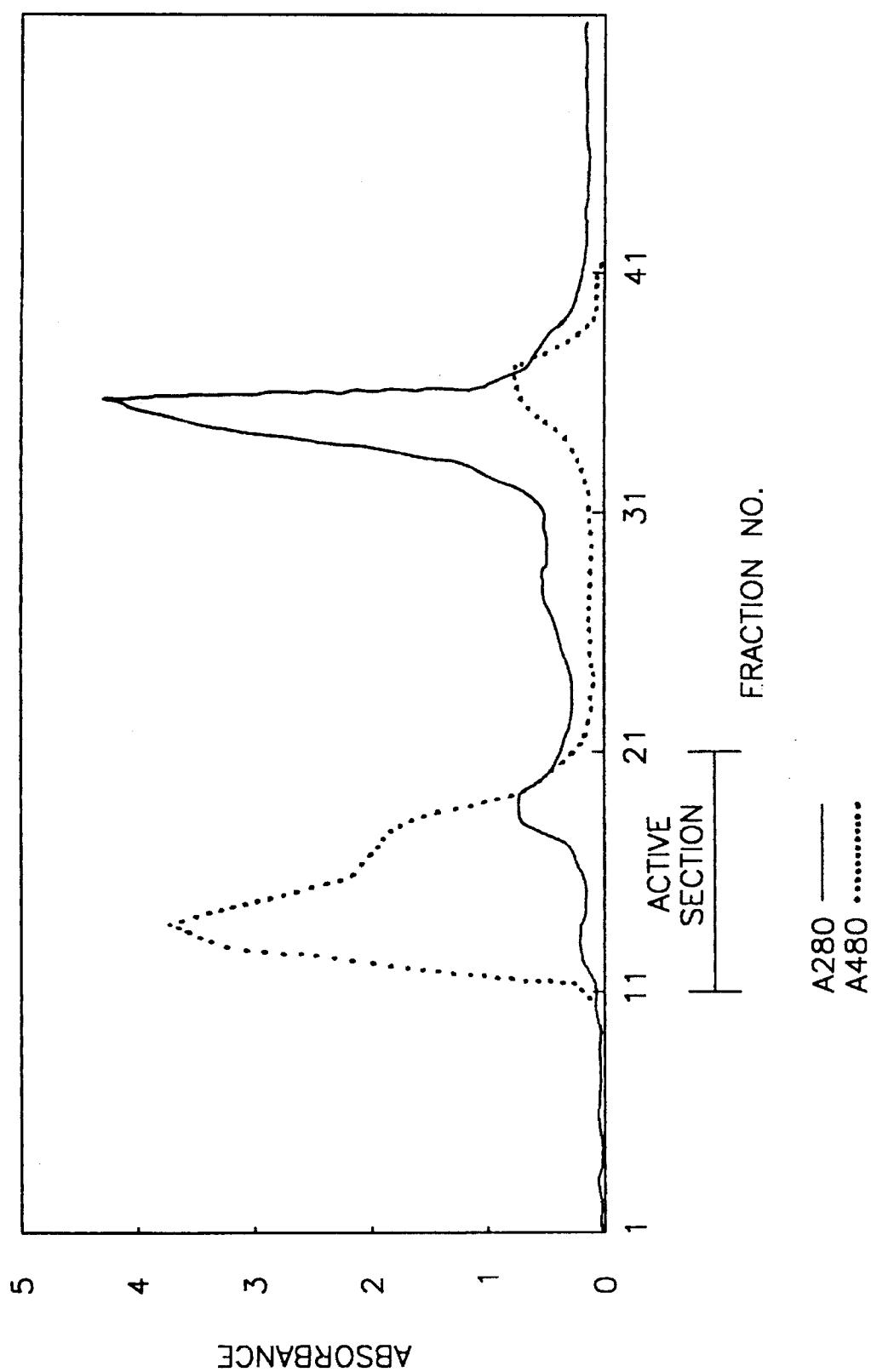
FIG. 1 illustrates graphs showing the absorbances at wavelengths of 280 and 480 nm ($A_{280}$ and $A_{480}$) in relation to the fractions as fractionated by the gel filtration chromatography in Example 1.

Then, the concentrate was charged into a column (11 cm×45 cm) packed with HP-20 (4 liters, manufactured by Mitsubishi Chemical Industries); while utilizing water as an equilibrating and developing solution, respectively, chromatography was carried out at room temperature, and the freely passed effluent fraction and water-washed fraction (non-adsorbed) were recovered. The column was washed with 50% methanol and acetonitrile, respectively, followed by replacement entirely with water for recycled use. The above non-adsorbed fraction was treated three times by the same procedure to give a completely non-adsorbed fraction (55 liters). The entirely non-adsorbed fraction was subjected to ultrafiltration for concentration by use of a ultrafiltration device type SEP-1013 (supplied by Asahi Chemical Industries) equipped with a ultrafiltration membrane with a molecular-weight cutoff of 3,000 to give a effluent solution (with a molecular weight of less than about 3,000, referred to as "SEP-OUT") and non-effluent adsorbed solution (with a molecular weight of not less than about 3,000, referred to as "SEP-IN"). The concentrated non-effluent adsorbed solution (SEP-IN) was poured into a column (1.5 cm×100 cm) packed with Bio-Gel p-60 equilibrated with water, and chromatography was conducted with water being used as a developing solution. Monitoring was done provisionally by measurement of absorbance at a wavelength of 280 nm, wherein a graph was drawn by plotting the measured absorbances as the ordinate against the fraction numbers as the abscissa, and the total sugar contents were measured mainly with the fractions not showing absorption, with the results being indicated in the same figure (FIG. 1).

The objective polysaccharides were obtained from the fractionated solutions (AF) of Fraction Nos. 11 to 22, followed by lyophilization to give a powdered product (30 g, Lot No. A).

The resulting purified polysaccharides were tested for characterization in accordance with the testing methods as mentioned previously, with the following characteristic properties being determined:

1) A sugar content (the phenol-sulfuric acid method): 79%
   (1) Sugar composition

TABLE 1

Effects Of AF on the serum parameters

| | Cholesterol (mg/dl) | | Albumin (g/dl) | | A/G ratio | | MDA (nmol/ml) | |
|---|---|---|---|---|---|---|---|---|
| | Day 14 | Day 21 | Day 14 | Day 21 | Day 14 | Day 21 | Day 14 | Day 21 |
| Normal | 50 | 52 | 4.10 | 4.16 | 1.63 | 1.67 | 2.7 | 2.5 |
| Control (PA) | 356 ± 13 | 167 ± 10 | 3.45 ± 0.05 | 4.11 ± 0.09 | 0.81 ± 0.05 | 1.49 ± 0.06 | 35.3 ± 2.1 | 16.1 ± 2.8 |
| AF (40 mg/kg) | 138 ± 17** | 93 ± 3** | 3.58 ± 0.09 | 3.92 ± 0.08 | 1.39 ± 0.04* | 1.74 ± 0.10** | 12.4 ± 1.4** | 11.4 ± 0.8** |
| AF (10 mg/kg) | 189 ± 17** | 96 ± 8** | 3.57 ± 0.08 | 4.02 ± 0.07 | 1.23 ± 0.08* | 1.73 ± 0.09** | 13.3 ± 3.2** | 10.2 ± 1.5** |

Note:
A/G = Albumin/[(Total serum protein) - (albumin)].
*$p < 0.05$.
**$p < 0.005$, significantly different from control.

TABLE 2

Effects of AF on the serum parameters

| After i.m. inject | Cholesterol (mg/dl) | | Albumin (g/dl) | | A/G ratio | | MDA (nmol/ml) | |
|---|---|---|---|---|---|---|---|---|
| | Day 14 | Day 21 | Day 14 | Day 21 | Day 14 | Day 21 | Day 14 | Day 21 |
| Normal | 40 | 48 | 4.10 | 4.16 | 1.63 | 1.67 | 2.7 | 2.5 |
| Control (PA) | 365 ± 23 | 173 ± 11 | 3.07 ± 0.09 | 3.39 ± 0.09 | 0.81 ± 0.05 | 1.06 ± 0.06 | 34.4 ± 2.1 | 16.3 ± 1.7 |
| AF (2.5 mg/kg) | 154 ± 53** | 77 ± 13** | 3.48 ± 0.09 | 4.41 ± 0.11 | 1.17 ± 0.07** | 1.93 ± 0.10** | 13.2 ± 1.6** | 7.9 ± 1.3** |
| AF (0.5 mg/kg) | 297 ± 34 | 168 ± 31 | 3.24 ± 0.13 | 4.10 ± 0.14 | 1.01 ± 0.06 | 1.60 ± 0.22 | 26.1 ± 3.5 | 14.5 ± 1.1 |

Note:
A/G ratio = Albumin/[(Total serum protein) - (albumin)].
*$p < 0.05$.
**$p < 0.005$, significantly different from control.

A uronic acid content: 62% (the m-hydroxydiphenyl method).

A neutral sugar content: 17% (the alditol acetate GC-MS method).

(2) Neutral sugar composition (the alditol acetate GC-MS method)

A glucose content: 5.5%

A galactose content: 39.7%

An arabinose content: 44.6%

A mannose content: 5.5%

A rhamnose content: 4.7%

(3) Miscellaneous sugars:

Aminosaccharides, aldohexoses and 2-deoxy-sugars were not contained.

Figure 2:
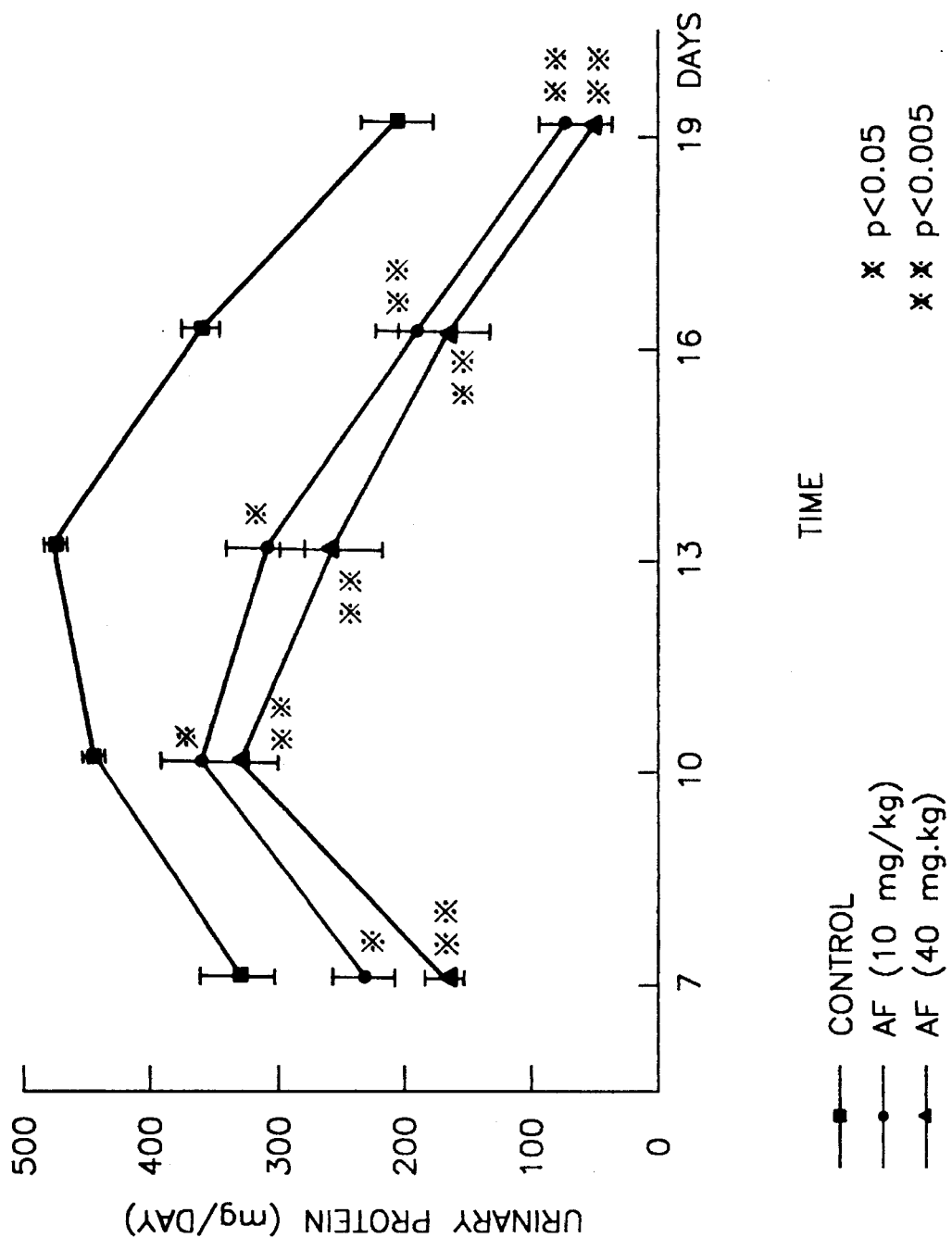
FIGS. 2 and 3 are graphs showing time-course changes in excretions of urinary protein in Example 1 where the polysaccharides (AF) of the present invention were given nephrotic syndrome model rats orally at different doses.
Figure 3:
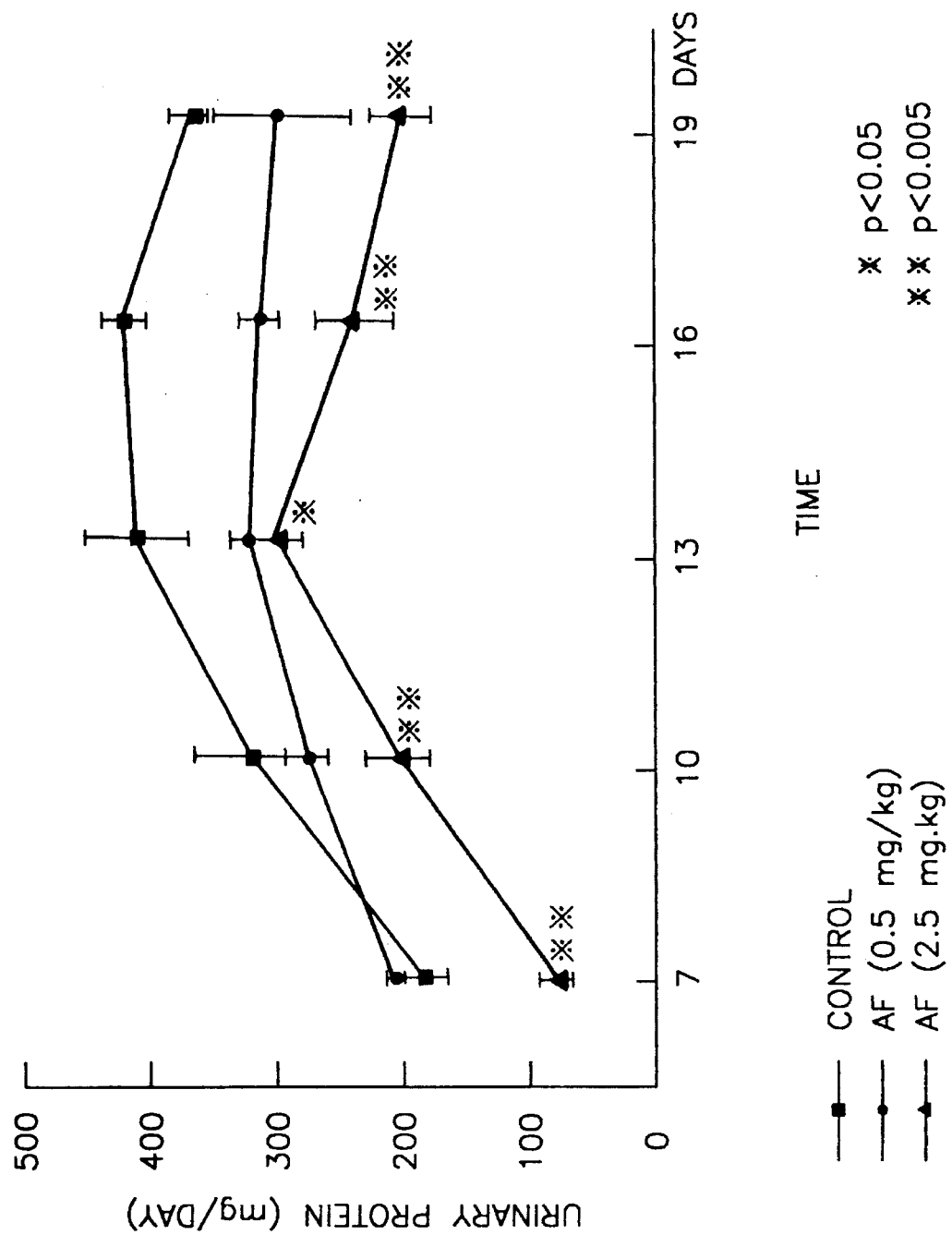

2) Molecular weight:

9,000 (standard polysaccharide: amylase kit, molecular weight, 100 to 360 K). p0 3) Assessment with the nephrotic syndrome model rats The purified test sample (AF), when administered the rats orally at doses of 10 mg/kg and 40 mg/kg and intramuscularly at doses of 0.5 mg/kg and 2.5 mg/kg, caused significant suppression of discharge of proteinuria individually, as shown in FIGS. 2 and 3. As tabulated in Tables 1 and 2, the significant improving effects were observed in the serum cholesterol level, serum albumin level and A/G ratio and serum peroxylipid (MDA) level.

4) Assessment with the carbon-tetrachloride induced liver injury model rats

As shown in Table 3, the purified test sample (AF), when administered to the rats orally at doses of 7 mg/kg and 35 mg/kg and intramuscularly at doses of 0.3 mg/kg and 1.5 mg/kg, respectively, suppressed an increase in the serum GOT and GPT levels in the dose dependent manner. Refer to Table 3.

TABLE 3

Effects of AF on serum transaminase

| | Transaminse (U/L) | |
|---|---|---|
| Animal group | GOT | GPT |
| Normal | 53 ± 3** | 29 ± 2** |
| Control (CCl$_4$) | 3800 ± 913 | 1870 ± 401 |
| CCl$_4$ + AF (7 mg/kg, p.o.) | 3296 ± 325 | 1485 ± 142 |
| CCl$_4$ + AF (35 mg/kg, p.o.) | 2210 ± 818* | 956 ± 234* |
| CCl$_4$ + AF (0.3 mg/kg, i.m.) | 1540 ± 345* | 858 ± 194* |
| CCl$_4$ + AF (1.5 mg/kg, i.m.) | 965 ± 303* | 484 ± 152* |

*$p < 0.05$
**$p < 0.005$, significantly different from control

EXAMPLE 2

Different lots of Salviae miltiorrhizae Radix raw materials were purified individually by the procedure as described in Example 1 to produce 3 lots of the purified products (Lot Nos. B, C and D) other than the one as described in Example 1, which were evaluated for their characteristic properties.

1) Sugar content (the phenol sulfuric acid method):

Lot No. B, 65%

Lot No. C, 80%

Lot No. D, 93%

(1) Sugar composition

Refer to Table 4.

(2) Neutral sugar composition (the alditol acetate GC-MS method)

Refer to Table 5.

(3) Miscellaneous sugars:

Neither of Lot Nos. B, C and D contained any of amino sugars, aldohexoses and 2-deoxy-sugars.

2) Molecular weight: (standard sugar: amylose kit, with Molecular weights of 100 to 360K).

Lot No. B, 150,000

Lot No. C, 280,000

Lot No. D, 250,000.

3) Assessment with nephrotic syndrome model rats

Lot Nos. B, C and D Were assessed for their efficacies, with the result that there were obtained the effects almost equivalent to the one in Example 1.

TABLE 4

| Lot No. | Sugar composition | | |
|---|---|---|---|
| | B | C | D |
| Content of uronic acid* | 55% | 65% | 75% |
| Content of neutral sugars** | 12% | 15% | 25% |

Notes:
*determined in accordane with the m-hydroxy-diphenyl method.
**determined in accordance with the alditol acetate GC-MS method.

TABLE 5

| Lot No. | Neutral sugar composition | | |
|---|---|---|---|
| | B | C | D |
| Content of glucose | 2.5% | 7.0% | 13.0% |
| Content of galactose | 28.0% | 42.0% | 50.0% |
| Content of arabinose | 35.0% | 48.0% | 55.0% |
| Content of mannose | 2.0% | 7.0% | 12.0% |
| Content of rhamnose | 1.5% | 7.3% | 12.5% |

EXAMPLE 3

For the purpose of investigation into whether or not the activity is essentially attributed to the sugar and to what an extent uronic acid is involved in the efficacy, the purified product of the present invention was subjected to oxidation and reduction by the following procedures, and the oxidation and reduction products were examined individually for their effects by giving rats with nephrotic syndrome model and rats with liver injury model the reaction products orally at a dose of 40 mg/kg and intramuscularly at doses of 40 mg/kg and 1.5 mg/kg, respectively.

(1) Oxidation (in accordance with the method as described in Noble, D. W. and Sturgeon, R. J., (1970), Carbohyd., Res., 12, 448):

A 600 mg quantity of the purified product was dissolved in 150 ml of distilled water, to which 150 ml of 0.2M sodium periodate solution was added to allow the reaction to proceed at 37° C. for 240 hours. After 150 ml of ethylene glycol was added to suspend the reaction, 500 mg of sodium borohydride was added to the reaction mixture, which was treated at room temperature for 24 hours, followed by suspension of the reaction with added acetic acid. The reaction solution was dialyzed with water, and the dialysate was lyophilized.

(2) Reduction (in accordance with the method s described in Taylor, R. L. and Conrad, H. E. (1972) Biochemistry, 11, 1383–1388).

A 50 mg quantity of the purified product was dissolved in distilled water, and after 249 mg of EDC (1-ethyl- 3-(dimethylaminopropyl)carbodiimide was added, and the reaction solution was subjected to reaction for 19 hours while being maintained at pH 4.75 with 0.1N hydrochloric acid. Thereafter, 10 ml of 2M sodium borohydride solution was added dropwise to the solution over the 1-hour period, while maintaining the solution at pH 7. followed by stirring for another 1 hour, dialysis and lyophilization.

Figure 4:
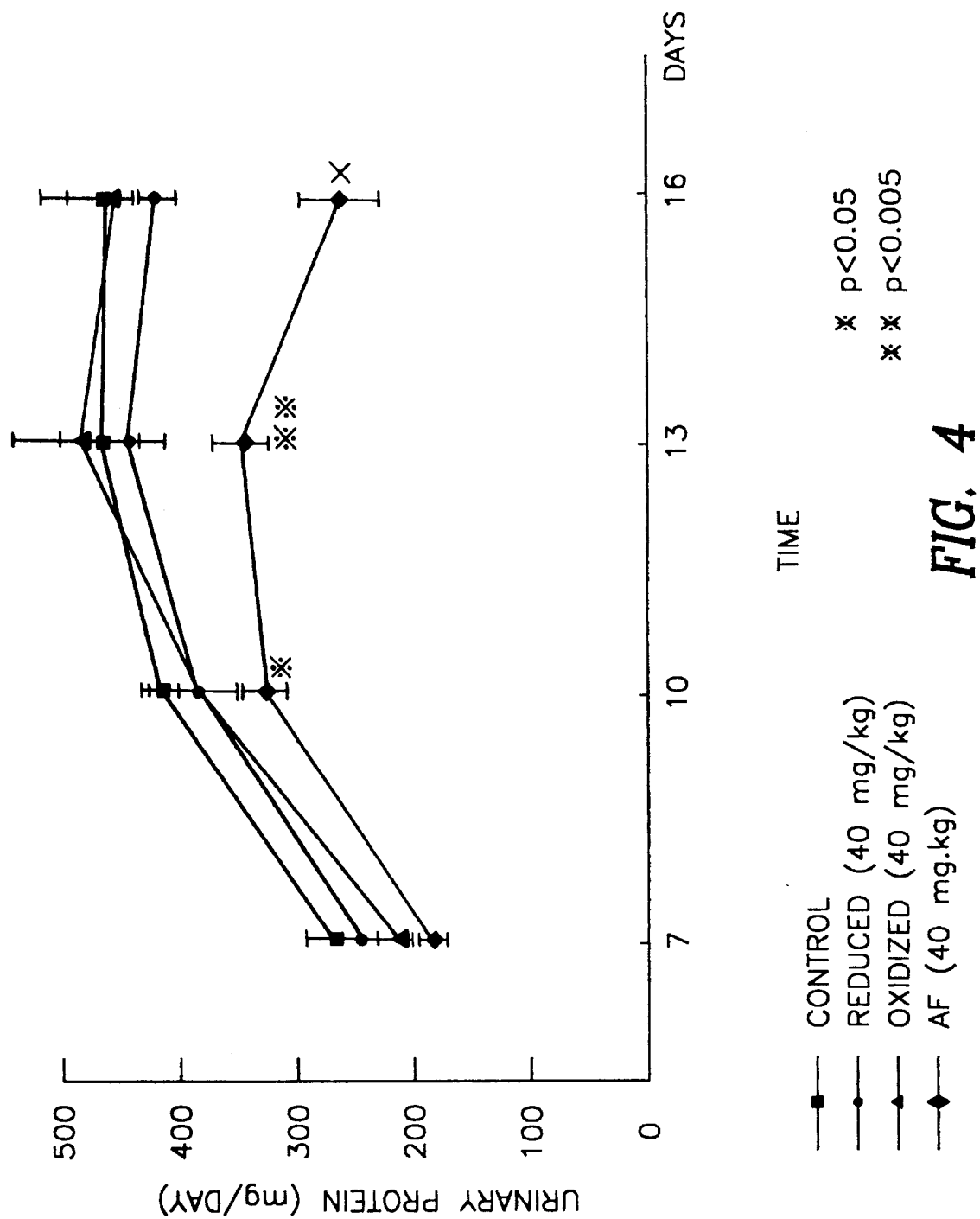
FIG. 4 illustrates graphs showing time-course changes in excretions of urinary protein after similar administration of the oxidized and reduced AFs, respectively.

The results, as shown in FIG. 4 and Tables 6 and 7, indicate that the oxidized and reduced samples exhibited no effect at all, suggesting that the active substance in the purified sample constitutes polysaccharides and is based largely on uronic acid. Comparison of the neutral sugar contents before and after reduction demonstrates that uronic acid contained in the present sample consists almost exclusively of galacturonic acid. Refer to FIG. 4 and Tables 6 and 7.

TABLE 6

Effects of AF as well as its oxidized and reduce products on serum parameters

| | Cholesterol (mg/dl) | Albumin (g/dl) | A/G ratio |
|---|---|---|---|
| After injection | 14 | 14 | 14 |
| Normal | 92 | 5.05 | 2.91 |
| Control (PA) | 442 ± 23 | 3.61 ± 0.05 | 1.63 ± 0.18 |
| AF (40 mg/kg) | 289 ± 45** | 4.13 ± 0.09** | 2.22 ± 0.11** |
| Oxidized AF (40 mg/kg) | 427 ± 24 | 3.91 ± 0.07 | 1.72 ± 0.24 |
| Reduced AF (40 mg/kg) | 427 ± 36 | 3.56 ± 0.03 | 1.77 ± 0.22 |

Notes:
A/G = (Albumin)/[(total serum protein) - (albumin)]
*;$p < 0.05$.
**;$p < 0.005$, significantly different from control.

TABLE 7

Effects of oxidized and reduced AFs on serum transaminase

| | Transaminse (U/L) | |
|---|---|---|
| Animal group | GOT | GPT |
| Normal | 62 ± 7** | 30 ± 4** |
| Control (CCl$_4$) | 4320 ± 422 | 2800 ± 364 |
| CCl$_4$ + AF(1.5 mg/kg i.m.) | 1020 ± 214** | 732 ± 180** |
| CCl$_4$ + reduced AF (35 mg/kg i.m.) | 2921 ± 912 | 2039 ± 462 |
| CCl$_4$ + oxidized AF (0.3 mg/kg i.m.) | 2760 ± 148* | 1800 ± 168* |

*$p < 0.05$
**$p < 0.005$, significantly different from control.

EXAMPLE 4

Since it was found in example 3 that D-galacturonic acid is of vital importance to the activity of the present product, pectic acid of plant origin having the polygalacturonic acid skeleton was assessed for its effects with the puromycin-induced nephrosis and carbon-tetrachloride induced liver injury models.

Pectinic acid was given rats with nephrotic model orally at doses of 10 and 40 mg/kg and intramuscularly at a dose of 2.5 mg/kg, respectively, followed by determination of excreted amount of urinary protein and serum cholesterol and albumin levels, while it was administered to rats with liver injury model intramuscularly at a dose of 1.5 mg/kg to determine the serum GOT and GPT levels.

The results, as tabulated in Tables 8, 9 and 10, revealed that pectinic acid when given intramuscularly suppressed significantly urinary protein excretion in the nephrotic syndrome model and even after oral administration, displayed the improving tendency. Also, pectinic acid revealed a conspicuous amelioration in the serum parameters in the cases of oral and intramuscular administration, In the case of oral administration, AF was shown to be more effective than pectinic acid in any of such indices.

Pectinic acid exhibited the same degree of efficacy against hepatitis as AF, and suppressed significantly increases in the serum GOT and GPT levels.

From the above-described results, it was shown that not only polysaccharides (AF) originated from Tanjin but also polysaccharides of different origins having the poly-D-galacturonic acid skeleton possess similar effects. Refer to Tables 8, 9 and 10.

TABLE 8

Effects of pectic acid on the urinary protein excretion

|  | Urinary protein excretion (mg/day) |
| --- | --- |
| Control (PA) | 478 ± 48 |
| Pectic acid (2.5 mg/kg i.m.) | 187 ± 28* |
| Pectic acid (10 mg/kg p.o.) | 346 ± 50 |
| Pectic acid (40 mg/kg p.o.) | 312 ± 65 |

Notes:
*$p < 0.05$, significantly different from control.

TABLE 9

Effects of pectic acid on serum parameters

|  | Cholesterol (mg/dl) | Albumin (g/dl) |
| --- | --- | --- |
| Control (PA) | 394 ± 13 | 3.00 ± 0.06 |
| Pectic acid (2.5 mg/kg i.m.) | 215 ± 19* | 3.26 ± 0.37 |
| Pectic acid (10 mg/kg p.o.) | 262 ± 42* | 3.30 ± 0.21 |
| Pectic acid (40 mg/kg p.o.) | 234 ± 56* | 3.30 ± 0.31 |

*$p < 0.05$, significantly different from control.

TABLE 10

Effects of pectic acid on serum transaminase

| Animal group | Transaminse (U/L) | |
| --- | --- | --- |
|  | GOT | GPT |
| Normal | 52 ± 3 | 28 ± 2 |
| Control (CCl$_4$) | 4388 ± 562 | 2328 ± 221 |
| CCl$_4$ + Pectic-acid (1.5 mg/kg i.m.) | 520 ± 180** | 292 ± 94** |

**$p < 0.005$, significantly different from control.

What is claimed is:

1. A water-soluble polysaccharide which is extracted from Tanjin with water or an aqueous solvent and has the following characteristic properties:
A. Sugar content: 60 to 100%
 (1) Sugar composition:
   40 to 80% of uronic acid (composed almost entirely of D-galacturonic acid) and
   10 to 30% of neutral sugars
 (2) Neutral sugar composition:
   0 to 15% of rhamnose
   0 to 15% of glucose
   25 to 55% of galactose
   30 to 60% of arabinose
   0 to 15% of mannose
B. Molecular weight: 150,000 to 300,000.

2. A process for producing a polysaccharide as claimed in claim 1, wherein said process comprises extracting Tanjin with water or an aqueous solvent, passing a solution, as obtained by removing the residue from the extract, through a non-polar, porous polymeric resin, concentrating the eluate by means of ultrafiltration and then subjecting the concentrate to gel filtration chromatography.

3. A process as claimed in claim 2, wherein the extraction of Tanjin is carried out at a pH value of about 2 to about 8.

4. A process as claimed in claim 2, wherein the aqueous solvent is a buffer or an aqueous solution of salts.

5. A process as claimed in claim 2, wherein the extraction of Tanjin is conducted at a temperature of about 40° to about 100° C.

6. A method for remitting nephrotic syndrome of hepatopathy symptoms in a subject which comprises administering to the subject, orally or intramuscularly, an effective amount of a water-soluble polysaccharide having poly-D-galacturonic acid as an effective constituent and wherein the water-soluble polysaccharide has been extracted from Tanjin with water or an aqueous solvent and has the following characteristic properties:
a) Sugar content: 60 to 100%;
 1) Sugar composition:
   40 to 80% of uronic acid (composed almost entirely of D-galacturonic acid) and 10 to 30% to neutral sugars;
 2) Neutral Sugar Composition:
   0 to 15% of a rhamnose
   0 to 15% of glucose
   25 to 55% of galactose
   30 to 60% of arabinose
   0 to 15% of mannose
b) Molecular weight: 150,000 to 300,000.

7. A method according to claim 6, wherein the water-soluble polysaccharide is a pectic substance.

* * * * *